United States Patent [19]

Heimgartner et al.

[11] Patent Number: 5,316,912

[45] Date of Patent: May 31, 1994

[54] POLYACRYLIC HYDRAZIDES AND THEIR APPLICATIONS AS GLYCOPROTEIN REAGENTS

[76] Inventors: Urs Heimgartner, Höschgasse 70, 8008 Zürich; Branko Kozulic, Georg Kempfstrasse 7, 8046 Zürich; Klaus Mosbach, Rebbergstrass 83, 8102 Oberengstringen, all of Switzerland

[21] Appl. No.: 448,105

[22] Filed: Dec. 13, 1989

[30] Foreign Application Priority Data

Dec. 16, 1988 [GB] United Kingdom ............... 8829470

[51] Int. Cl.$^5$ .................. G01N 33/53; G01N 33/543
[52] U.S. Cl. ........................ 435/7.9; 435/7.92; 436/518; 436/530; 436/87; 436/804
[58] Field of Search ............... 435/7.9, 7.92, 7.94, 435/975; 436/518, 520, 521, 522, 529, 530, 87, 808

[56] References Cited

U.S. PATENT DOCUMENTS 4,778,751 10/1988 El Shami et al. ................ 436/504

OTHER PUBLICATIONS

Kozulic et al "Preparation of the stabilized glycoenzymes by cross-linking their carbohydrate chains" Chem. Abstracts 109(25):Abstract No 225585p (Dec. 1988).

Bayer et al "Enzyme-based detection of glycoproteins on blot transfers using avidin-biotin technology" Anal. Biochem. 161 pp. 123-131 (1987).

Kozulic et al. "Poly-N-acryloyl-Tris gels as anticonnection media for electrophoresis and isoelectric focusing" Anal. Biochem. 163 pp. 506-512 (1987).

Kozulic et al. "Electrophoresis of DNA restriction fragments in poly-N-acryloyl-Tris gels" Anal Biochem. 170 pp. 478-484 (May 1, 1988).

Heimgartner et al, "Polyacrylic Polyhydrazides as Reagents for Detection of Glycoproteins", *Analytical Biochemistry,* 181, 1989, pp. 182-189.

Heimgartner et al, "Polyacrylic polyhydrazides as novel reagents for detection of antibodies in immunoblotting assays", *Journal of Immunological Methods,* 132, 1990, pp. 239-245.

Miron et al, "Polyacrylhydrazido-Agarose: Preparation Via Periodate Oxidation and Use For Enzyme Immobilization and Affinity Chromatography", *Journal of Chromatography,* 215, 1981, pp. 55-63.

Bartles et al, "I-Wheat Germ Agglutinin Blotting: Increased Sensitivity with Polyvinylpyrrolidone Quenching and Periodate Oxidation/Reductive Phenylamination" Analytical Biochemistry, 140, 1984, pp. 284-292.

*Primary Examiner*—Esther L. Kepplinger
*Assistant Examiner*—Carol E. Bidwell
*Attorney, Agent, or Firm*—K. L. Orzechowski; Walter C. Farley

[57] ABSTRACT

A method for detecting a glycoprotein using a solid support is disclosed where the glycoprotein is oxidized by periodate, polyacrylic polyhydrazide which is a copolymer having repeating units possessing a hydrazide group and repeating units possessing hydroxyl groups is coupled to the oxidized glycoprotein and a glycoenzyme or radioactive compound containing aldehyde groups or activated ketone groups is coupled to the polyacrylic polyhydrazide which allows for detection of the glycoprotein. The glycoprotein may be directly attached to the solid support or may be bound to an antigen which is immobilized on the solid support.

14 Claims, 12 Drawing Sheets

FIG. 1A

● CARBOHYDRATE RESIDUE ▱ ALDEHYDE ▻ HYDRAZIDE
◂■ HYDRAZONE

FIG. 1B

● CARBOHYDRATE RESIDUE ▱ ALDEHYDE ▻ HYDRAZIDE
◂■ HYDRAZONE

FIG. IC

■ CARBOHYDRATE RESIDUE    ◻ ALDEHYDE    ◊ HYDRAZIDE
　　　　　　　　　▬ HYDRAZONE

FIG. ID

■ CARBOHYDRATE RESIDUE    ◻ ALDEHYDE    ◊ HYDRAZIDE
　　　　　　　　　▬ HYDRAZONE

1 STEP

2 STEP

POLYACRYLIC HYDRAZIDES AND THEIR APPLICATIONS AS GLYCOPROTEIN REAGENTS

FIELD OF THE INVENTION

This invention concerns polymeric hydrazides consisting of an aliphatic C—C backbone and side chains containing hydrazide and other hydrophilic groups. Such polyhydrazides were found to specifically react with the aldehyde groups generated in the sugar portion of a glycoprotein. Since immunoglobulins are also glycoproteins, the polyhydrazides were used to introduce a label into the antibody molecule. Therefore, the most important application of the polyhydrazides includes detection of antibodies of immunoassays and detection of glycoproteins in general.

BACKGROUND OF THE INVENTION

In many research, industrial and clinical laboratories there is a growing need for indentification of a single protein present in a complex protein mixture. This is most often achieved by one or two-dimensional electrophoretic separation of proteins followed by Western blotting. Here Western blotting includes transfer of proteins to a suitable membrane, reaction with antibodies specific for one particular protein and visualization of the antibodies bound to that protein. The visualization of antibodies is done in an indirect way, that is through a signal generated by a label attached to the antibody molecule. The label is very often an enzyme but other molecules producing a suitable signal, such as fluorescent dyes or radioactive compounds, are also in use. There are several ways to couple a label to an antibody, and the properties of the resulting conjugate are greatly dependent on the coupling method used for its preparation (reference 1).

In addition to detection of a single protein, it is sometimes necessary to identify a certain class of proteins. This can be achieved through a common determinant of these proteins. For example, glycoproteins can be detected through the carbohydrate chains that are covalently linked to the protein part of the molecule. Thus, the intact carbohydrate chains can be detected by means of proteins, such as lectins, glycosidases or glycosyltransferases, that recognize those monosaccharides that are present in the glycan chains (reference 2). A more general approach involves a modification of the carbohydrate chains followed by their detection through a group introduced by the modification. It is obvious that such a group must not be present in an intact protein or glycoprotein molecule. Aldehyde groups are easily and conveniently generated in the sugar chains, either chemically or enzymatically, and then detected by means of a hydrazide reagent and a suitable label (reference 2).

Antibodies, that is immunoglobulins, are also glycoproteins. Therefore, their carbohydrate chains can be used to introduce a label. This approach is very attractive because the carbohydrate chains of antibodies are apparently not directly involved in the binding of an antigen. Several reports have appeared describing preparation of such conjugates (references 3 and 4). In one report (references 5) it was claimed that an enzyme was coupled to the sugar portion of the antibody, but the procedure described was later found unsatisfactory (reference 6). We have found that aldehyde groups introduced into IgG can be used to cross-like the carbohydrate chains present on each of the two IgG heavy chains (reference 7). The cross-linking reaction by dihydrazide molecules was much more favorable than the reaction of dihydrazides through only one hydrazide group. This finding has indicated that it is difficult to introduce free hydrazide groups into IgG by using a dihydrazide. As demonstrated in this invention, that can be readily achieved by polymeric hydrazides which therefore serve as a bridge to the label.

OBJECTIVES OF THE INVENTION

It is an object of the present invention to provide a process for the preparation of polyacrylic hydrazides.

It is another object of the present invention to provide a process for coupling of polyacrylic hydrazides to oxidized glycoproteins in a solution and on a solid phase or support, such as a membrane.

It is another object of the present invention to demonstrate the use of polyacrylic hydrazides in detection of glycoproteins in general and of immunoglobulins in particular.

It is another object of the present invention to demonstrate detection of antigens through polyacrylic hydrazides coupled to antibodies.

SUMMARY OF THE INVENTION

We have found that suitable polyacrylic hydrazides are conveniently prepared through co-polymerization of a neutral, hydrophilic monomer and a monomer containing an activated ester group. Neutral monomers include acrylamide, N-acryloyl-tris-(hydroxymethyl)-aminomethane and N-acryloyl-2-amino-2-deoxy-D-glucitol, whereas N-acryloxysuccinimide was used as an activated monomer. The reaction of hydrazine with the copolymer produced the desired polyacrylic hydrazides. Such polyhydrazides couple readily to periodate oxidized glycoproteins, for example to horse radish peroxidase (HRP) and immunoglobulins. Detection of glycoproteins on solid support, such as membranes consists mainly of periodate oxidation of these glycoproteins and polyhydrazide mediated coupling of HRP to the modified glycoproteins. Staining on HRP activity then locates the glycoproteins. The coupling of HRP is carried out through the aldehyde groups generated in the carbohydrate chains of this glycoenzyme. The detection method provided in this invention is specific for glycoproteins and its sensitivity for highly glycosylated proteins is comparable to the sensitivity of Aurodye (Janssen) staining of the blots. Detection of antigens is performed through the antibodies which have been oxidized by periodate. The polyhydrazides serve as a bridge between the oxidized sugar chains of an antibody and the oxidized sugar chains of an glycoenzyme, such as horse radish peroxidase (HRP). This approach offers several advantages, such as the attachment of a label to the inert sugar chains of antibodies and the possibility to avoid the use of secondary antibodies.

In place of the enzyme (HRP) we have also used another label, such as a radioactive compound, in order to improve some properties of the method.

BRIEF DESCRIPTION OF THE DRAWINGS

FIGS. 4A-4C show specific detection of glycoproteins after electrophoretic separation and transfer to a membrane as described in Example 4 a;

DETAILED DESCRIPTION OF THE INVENTION

Various aspects of the present invention are illustrated by 7 examples and 8 figures.

EXAMPLE 1

Preparation of polyacrylamide polyhydrazide (PANPH).

The polyhydrazide was obtained from poly(acrylamide-co-N-acryloxysuccinimide) (PAN) whose synthesis is described in reference 8. Briefly, acrylamide (3.146 g) and N-acryloxysuccinimide (1.48 g) were dissolved in 35 ml of dry tetrahydrofurane and polymerized with 20 mg of azo-bis-(isobutyronitrile) at 55° C. for 24 h. The dried PAN was dissolved in 20 mM sodium acetate buffer, pH 4.5, at concentration of 2%. After cooling to 0° C., the solution was slowly added to ten times its volume of 1M hydrazide acetate in 0.2M sodium acetate, pH 5.7. After two hours, the polymeric hydrazide was purified directly by dialysis or it was first precipitated in ethanol. The precipitate was collected by centrifugation, immediately redissolved on 0.1 m sodium acetate, pH 4.5 and dialyzed against the same buffer. The resulting PANPH had a hydrazide content of 0.7–0.9 micromoles per mg dry polymer, as determined by trinitrobenzene sulfonic acid with adipic acid dihydrazide as a standard.

EXAMPLE 2

Preparation of Poly(N-acryloyl-tris-(hydroxymethyl)aminomethane-co-N-acryloxysuccinimide) (PNATN)

In a typical preparation, NAT (2.45 g, 14 mmole) prepared as described (reference 9) and N-acryloxysuccinimide (0.48 g, 2.8 mmole) were dissolved in 35 ml of dry dimethylformamide (DMF) in a 50 ml ampoule and degassed in vacuo. A stream of dry nitrogen was passed through the solution for 15 min and then azo-bis-(isobutyronitrile) (AIBN, 33 mg in 330 microliters of dry DMF) was added into the ampoule. The ampoule was quickly sealed and incubated in a water bath at 55° C. for 24 h. The resulting polymer is purified by precipitation in dry acetone or ethanol (ten times the volume of the polymer solution). The precipitate is collected by centrifugation and redissolved in 50 mM acetic acid and dialyzed against the same solution. The polymer can be stored at −20° C. or freeze-dried from the acetic acid solution.

b. Preparation of poly(N-acryloyl-tris(hydroxymethyl)-aminomethane)-polyhydrazide (PNATPH). PNATPH is prepared by addition of hydrazine to the PNATN purified as described under 2a or by addition of hydrazine to the polymer solution in DMF without previous purification of the polymer. In the first case, the procedure outlined under example 1 is followed. In the second case, at the end of polymerization the ampoule is cooled to −20° C. and carefully opened. A stream of dry nitrogen is immediately passed through the solution and anhydrous hydrazine, in five fold molar excess over N-acryloxysuccinimide and freshly diluted with DMF, is quickly added. The reaction mixture is stirred for about 30 min at 0° C. and then at room temperature. The resulting PNATPH was precipitated in ethanol and further treated as described for PANPH (Example 1). When the polyhydrazide was prepared with NAT and N-acryloxysuccinimide in molar ratio of 5:1, the PNATPH had a hydrazide content of 0.3–0.4 micromole/mg dry polymer. PNATPH solution can be stored for several weeks at +4° C. It can be stored for several months frozen at −20° C. for lyophilized from the sodium acetate buffer.

EXAMPLE 3

Preparation of poly(N-acryloyl-2-amino-2-deoxy-D-glucitol)polyhydrazide (PNAGAPH)

In a typical preparation, 0.7 g of N-acryloyl-2-amino-2-deoxy-D-glucitol (N-acryloyl-glucosaminitol, NAGA), prepared as described in reference 10, and 0.126 g of N-acryloxysuccinimide were dissolved in 5 ml of dry DMF. After degassing and flushing with nitrogen, 40 μl of AIBN (100 mg/ml) was added, the ampoule sealed and heated at 55° C. for 24 h. As described for PNATPH, the resulting polymer was either purified and then reacted with hydrazine or hydrazine was immediately added to the DMF solution of the polymer. In the latter case, the polymer precipitates but it can be readily dissolved in the acetate buffer.

EXAMPLE 4

Applications of polyhydrazides coupled to an enzyme in detection of glycoproteins a. The "two incubations protocol". FIG. 1 shows a scheme for detection of glycoproteins. A glycoprotein is immobilized on a solid support (membrane) and oxidized by periodate (panel 1). The oxidized glycoprotein is reacted with a polyhydrazide (panel 2) or another bifunction or multifunction hydrazide. Some of the hydrazide groups react with the aldehydes generated in the sugar chains of the immobilized glycoprotein, and some remain free. The free hydrazide groups are reacted with the aldehyde groups generated in the carbohydrate chains of a soluble glycoenzyme, such as peroxidase (panel 3). The bound enzyme (panel 4), and through it the immobilized glycoprotein, is located with a suitable substrate which is usually converted to a colored product by the enzyme.

FIG. 2 shows the results of experiments done to evaluate different hydrazide reagents for detection of glycoproteins. Onto each nitrocellulose strip, serial dilutions of pre-oxidized proteins (1 mg/ml protein, 10 mM sodium periodate, 1 h in the dark) were applied. Lane 1 always contains fetuin, lane 2 rabbit IgG, lane 3 human IgM and lane 4 an unglycosylated protein, E. coli beta-galactosidase, as a control. The remaining binding sites on all membranes, except that shown in panel A, were blocked by BLOTTO (reference 11). Staining of all proteins in panel A was done by Aurodye as described by the manufacturer. The membranes B-F were then incubated for 45 min with a hydrazide reagent in 0.1M acetate buffer pH 4.5. The membrane in panel B was incubated with 200 mM malonic acid dihydrazide, in panel C with 200 mM adipic acid dihydrazide, in panel D with 200 mM tricarblilic acid trihydrazide, in panel E with 0.8 mM PANPH (plus 3% bovine serum albumin) and in panel F with 0.8 mM PNATPH. The concentrations of the polyhydrazides are given as molarities of the hydrazide groups. The membranes were washed (3 times with the buffer) and subsequently incubated for 75 min with oxidized horse radish peroxidase at 5-10 $\mu$g/ml in 0.1M acetate buffer, containing 0.2M NaCl and 5% nonfat dry milk. The membranes were then washed three times with BLOTTO pH 7.5 and stained on peroxidase activity with 4-chloro-1naphtol (reference 12). The oxidized peroxidase used above was prepared by periodate oxidation of the enzyme (5-8 mg/ml in 0.1M acetate buffer pH 4.5, 8-10 mM NaIO$_4$, 2 h at 0° C. in the dark) and desalting by passing through a PD-10 column (Pharmacia).

As can be seen from FIG. 2 panel 1, practically equal quantities of the four proteins were applied to the membranes. Of these proteins, only human IgM is weakly stained with the two dihydrazides (panels B and C). The trihydrazide made possible detection of all glycoproteins (panel D), but IgG was stained very weakly. The polymeric hydrazides (panels E and F) stained strongly all glycoproteins, and a higher sensitivity is achieved by PNATPH (panel F). Under the conditions described, unspecific staining of the unglycosylated protein, beta-galactosidase in lane 4 of each panel, was not observed. The sensitivity of our staining procedure is for some proteins (fetuin and IgM) similar to that of Aurodye staining (panel A versus panel F).

We have varied many parameters of the glycoprotein staining procedure outlined above. Thus, polyacrylamide polyhydrazides of different size and hydrazide group concentration were prepared or purchased (Sigma). Polyacrylamide polyhydrazides have a general tendency to produce a higher background and they show a higher unspecific binding to unglycoslyated proteins than PNATPH. This tendency is stronger for the high molecular weight polyacrylamide polyhydrazides. Therefore, we have prepared the PANPH (Example 1), an acrylamide based polymer that is expected to be of medium size (i.e., below 10 kDa) because the starting product (PAN, reference 8) is of that size. PANPH polymers of different size were evaluated. We have found that longer PANPH polymers (separated from the shorter ones by ultrafiltration through a PM-30 membrane) give a stronger signal but also a higher background. Accordingly, the longest polymers producing acceptable background should be used for maximal sensitivity. On the other hand, PNATPH polymers always showed less background staining. We assume that this property of PNATPH is related to its more hydrophillic character, coming from the presence of three hydroxyl groups in every repeating unit.

We have also prepared an extremely hydrophilic polyhydrazide, PNAGAPH (Example 3), containing 5 hydroxyl groups in every repeating unit.

FIG. 3 shows the glycoprotein staining done with PNAGAPH. In all panels lane 1 contains fetuin, lane 2 rabbit IgG and lane 3 beta-galactosidase, in concentrations given in FIG. 2. The other conditions are also identical to those described for FIG. 2. Panels A and B were incubated with the PNAGAPH prepared from the purified activated polymer, whereas panels C and D were incubated with the PNAGAPH prepared from the activated polymer in DMF (see Example 3). Panels A and C were incubated for 30 min and panels B and D for 3 h.

The background staining in FIG. 3 is not visible even after a rather long incubation (3 h), in contrast to the membranes incubated with PNATPH or PANPH (not shown). From this result we conclude that polymeric hydrazides should be as hydrophilic as possible.

In addition to type and size of the polyhydrazides, we have investigated many parameters that might have an impact on the performance of the glycoprotein staining procedure. Thus, the concentration of the polymeric hydrazide was also important. Optimal results were observed with 0.8 mM hydrazide groups of PANPH and PNATPH. Lower concentrations (below 0.1 mM) give a weaker signal, and higher concentration (5 mM) much higher background.

We have also found that oxidation conditions influence the staining sensitivity. Thus, at a low periodate concentration the oxidation at pH 4.5 results in a much stronger signal than the oxidation at pH 7.5. Incubation time can be lowered by increasing the polyhydrazide concentration, but the appearance of background was difficult to prevent, except with PNAGAPH. An increase in ionic strength of the PNATPH solution reduces background, but this was not the case with PANPH.

In order to reduce both background and unspecific staining, The PANPH needs to be incubated in presence of a protein, such as bovine serum albumin. On the other hand, there is no need for addition of a protein to PNATPH and PNAGAPH solution, since these two polyhydrazides show negligible unspecific binding.

The coupling of polyhydrazides to oxidized glycoproteins is conveniently carried out at pH values from 3.5 to 5.5. Higher values may be used, but the sensitivity is lower. This is in agreement with the previous findings (reference 13).

The concentration of oxidized peroxidase can be increased without causing a higher background. The incubation time is then shorter, but more enzyme is spent. The oxidized peroxidase loses very slowly its activity in BLOTTO, 50% in three to four weeks.

We have further used the "two incubations protocol" for detection of glycoproteins after SDS electrophoretic separation and transfer to a polyvinyldenedifluoride (PVDF) membrane (Millipore). The proteins were separated in a 5-20% polyacrylamide gradient gel according to reference 14. The transfer of proteins to the membrane was carried out as described in reference 15.

The silver staining of the polyacrylamide gel was done as in reference 16.

Figure 1A:
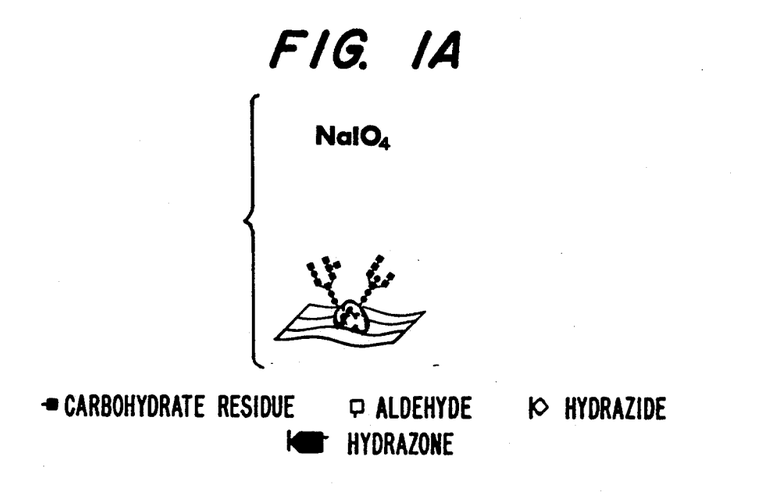
FIGS. 1A–1D are a schematic presentation of the glycoprotein detection method of the present invention showing the steps of reacting a glycoprotein bound to a membrane by periodate, incubating the membrane in a solution containing the polyacrylic polyhydrazide, binding an oxidized glycoenzyme to the remaining hydrazide groups and visualizing the enzyme after incubation with its substrate.
Figure 1B:
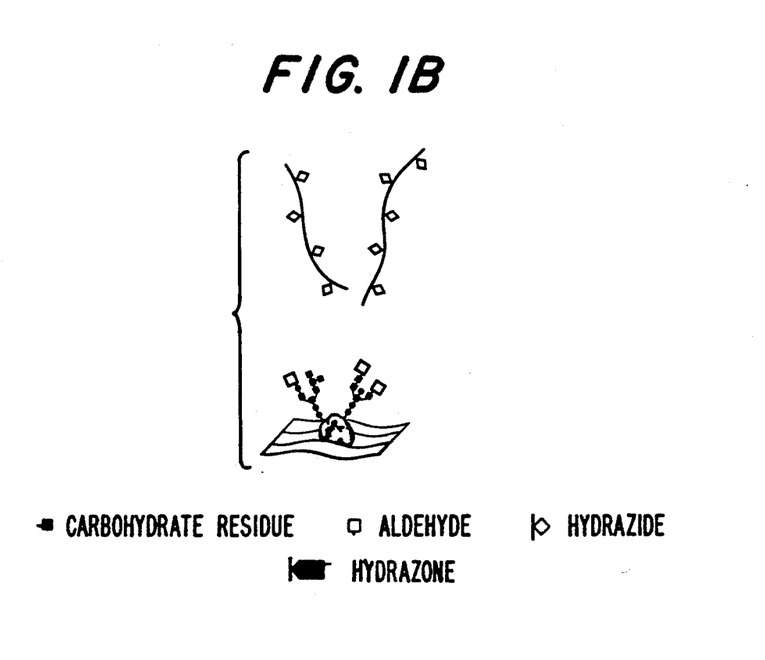
Figure 1C:
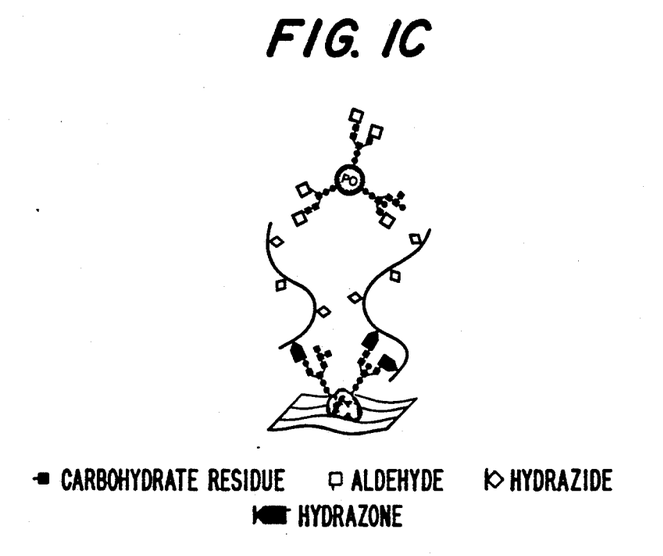
Figure 1D:
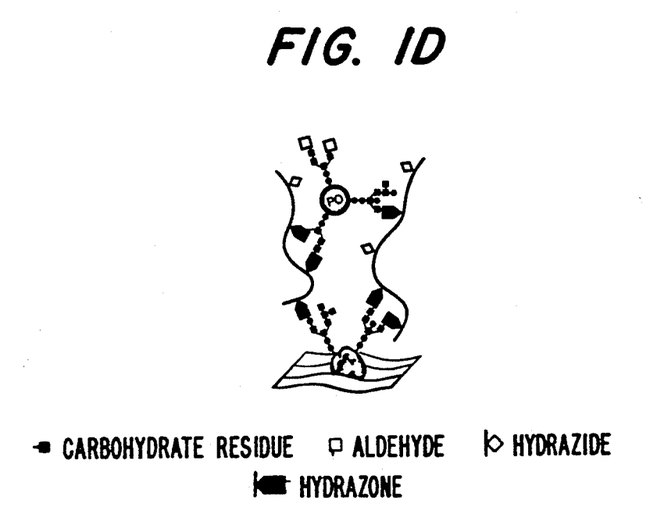
Figure 2A:
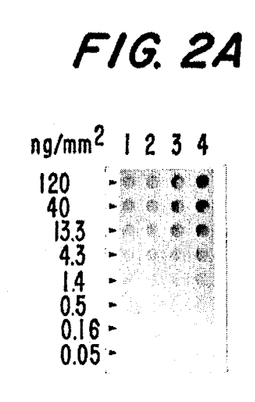
FIGS. 2A-2F show the results of evaluation of different hydrazides for detection of glycoproteins using the method of the present invention.
Figure 2B:
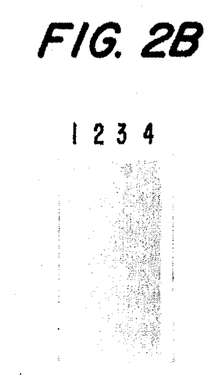
Figure 2C:
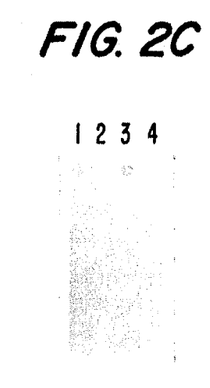
Figure 2D:
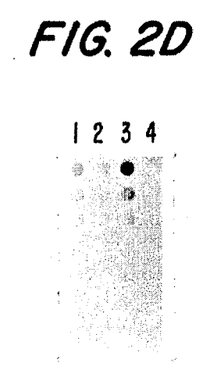
Figure 2E:
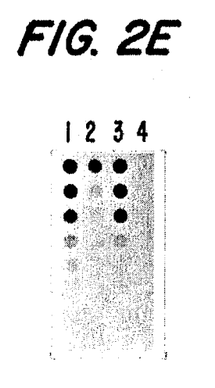
Figure 2F:
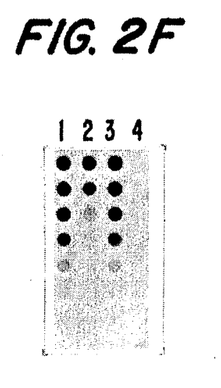
Figure 3A:
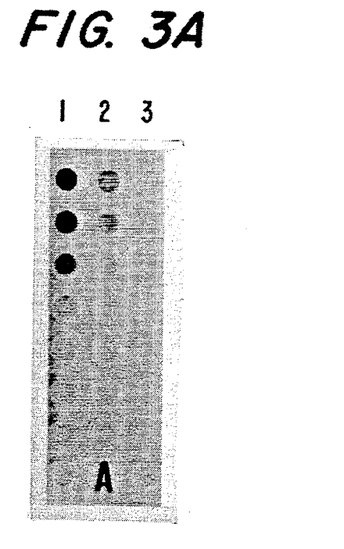
FIGS. 3A-3D show glycoprotein detection using the method of the present invention with poly(NAGA) polyhydrazide as described in Example 4.
Figure 3B:
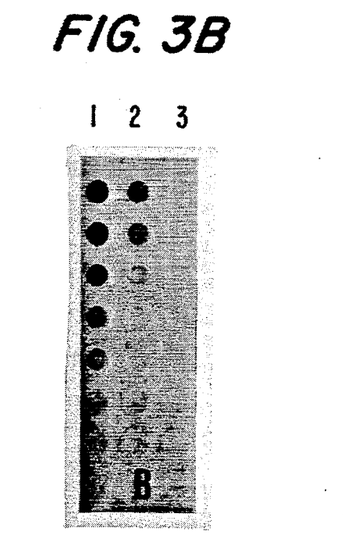
Figure 3C:
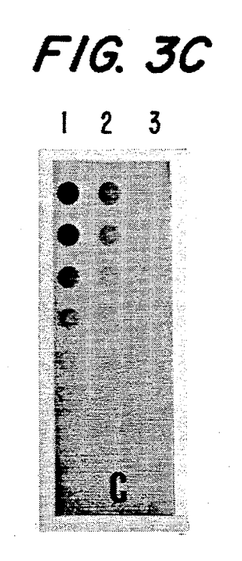
Figure 3D:
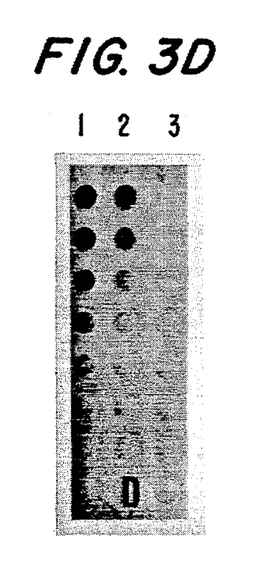
Figure 4A:
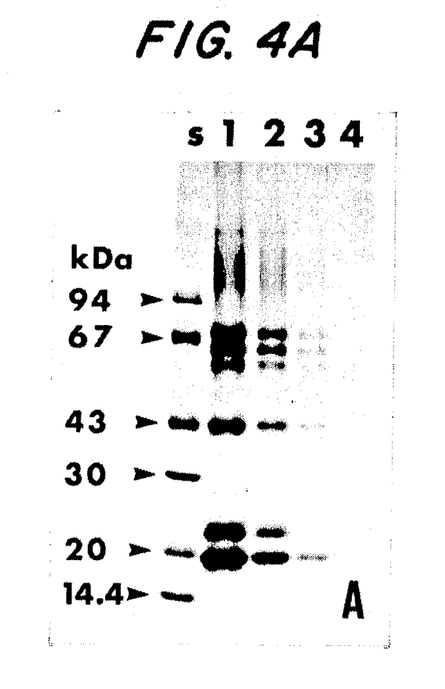
Figure 4B:
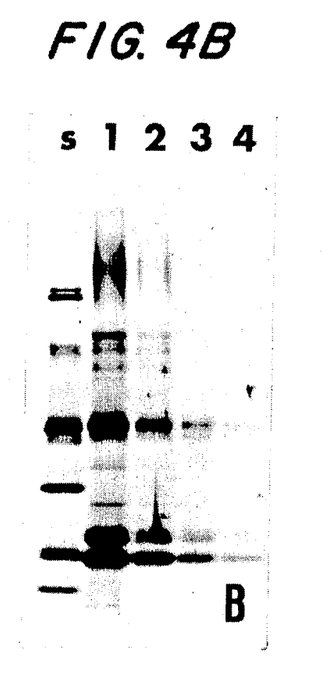
Figure 4C:
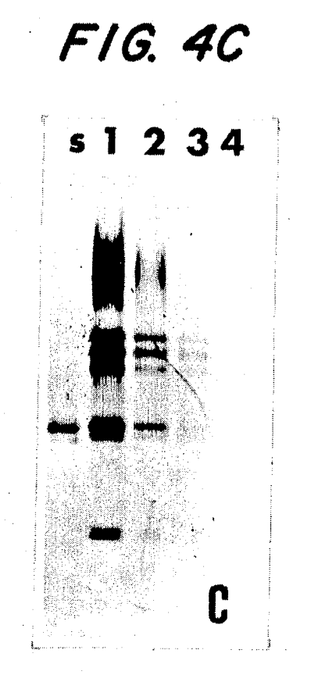

FIG. 4 shows a polyacrylamide gel stained with silver (panel A), a PVDF membrane stained with Aurodye (panel B) and a PVDF membrane stained for glycoproteins according to our "two incubations protocol". The same proteins are shown in all three gels. In lane s, there are low molecular weight standard proteins from Pharmacia. They include: phosphorylase b (94 kDa), bovine serum albumin (67 kDa), ovalbumin (43 kDa), carbonic anhydrase (30 kDa), soybean trypsin inhibitor (20 kDa) and lactalbumin (14.4 kDa). In lanes 2-4 different amounts of the same glycoprotein mixture were applied. The glycoproteins are: invertase (the diffuse band above 94 kDa), fetuin (the three bands around 67 kDa), ovalbumin (43 kDa) and ribonuclease B (about 22 kDa) containing some ribonuclease A (about 20 kDa). Lane 1 contains 750 ng of each protein, lane 2 250 ng, lane 3 80 ng and lane 4 30 ng.

The membrane C was oxidized with 10 mM $NaIO_4$ in 0.1M sodium acetate buffer, pH 4.5 at room temperature for 30 min. It was then incubated with PNATPH followed by oxidized peroxidase and staining on peroxidase activity, as described for FIG. 2.

FIG. 4 shows that the glycoprotein staining procedure described in this invention is characterized by a sensitivity similar to that of silver and Aurodye staining (panel A and B versus panel C). Such a high sensitivity was not achieved by any of the published procedures. The selectivity of the staining is also remarkable, since of all standard proteins in lane s only the glycoprotein ovalbumin is stained. In addition, the nonglycosylated form of ribonuclease (ribonuclease A) is not stained.

b. The "one incubation protocol".

This procedure differs from the one described in FIG. 1 only in one important detail, that is the steps 2 and 3 are combined into one step. Thus, an oxidized glycoprotein on a solid support is incubated with a glycoenzyme-polyhydrazide conjugate, which is prepared as describe below.

In general, PANPH or PNATPH are coupled to periodate oxidized HRP. The coupling reaction is straightforward (as checked by SDS electrophoresis), but purification of the conjugate is rather complicated because polyhydrazides behave also as charged macromolecules. Several examples describing preparation of such conjugates are given below.

In one experiment, a fraction of PANPH that passed through the PM-30 ultrafiltration membrane was used. After coupling the conjugate was purified from the unbound polyhydrazide by several concentration-dilution cycles.

In the second experiment, PANPH was treated with hydrazine in the presence of a water soluble carbodiimide in order to block all carboxyl groups on the polymer. Since the resulting polymer does not bind to an anionic ion exchanger (Mono Q), the conjugate was bound to a column packed with this ion exchanger (10 mM piperazine buffer, pH 10.2) and eluted with 50 mM piperazine-HCl buffer, pH 8.0 containing 0.2M NaCl.

In the third experiment, the purification was attempted over a Concanavalin A-Sepharose column. However, about 90% of the conjugate did not bind and the portion that bound could be hardly released from the column.

Finally, we have found that purification of the conjugate may not be necessary. When periodate oxidized HRP (2 mM $NaIO_4$ for 2 h at 0° C.) was incubated at 1 mg/ml with PNATPH which was 1-4 mM in hydrazide groups, the formed conjugates could be directly used for detection of glycoproteins.

Figure 5A:
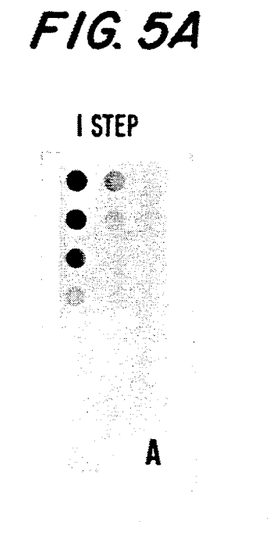
FIGS. 5A-5B show specific detection of glycoproteins according to the method depicted in FIG. 1 (panel B) and using a polyacrylic polyhydrazide-peroxidase conjugate (panel A) prepared as described in Example 4 b.
Figure 5B:
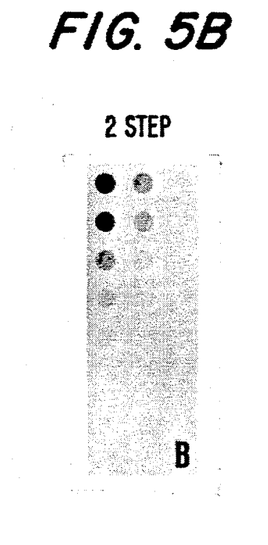

FIG. 5 shows glycoproteins on a membrane stained according to the "one incubation protocol" (panel A) and according to the "two incubations protocol" (panel B). Lane 1 contains fetuin, lane 2 rabbit IgG and lane 3 beta-galactosidase. The incubation conditions were essentially as described for FIG. 2. The conjugate used in the "one incubation protocol" was not purified.

This figure shows that the sensitivity of the "two incubations protocol" is higher. We have obtained such a result in all instances, regardless whether and how the HRP-polyhydrazide conjugate was purified prior to its use in the "one incubation protocol".

EXAMPLE 5

Application of polyhydrazides in detection of antigens

As demonstrated by previous examples, polyhydrazides can act as a bridge that links the oxidized carbohydrate chains of two glycoproteins. When one of them is an antibody and the other an enzyme, the conjugate can be used for detection of an antigen.

The conjugates can be prepared as described by examples a-e and example f.

a. Goat antibody (against guinea pig immunoglobulins) is oxidized by periodate (10 mM, 2 h), desalted and incubated overnight with an oxidized peroxidase-PNATPH conjugate (1 mg/ml peroxidase plus 1.5 mM hydrazide). The molar ratio of IgG to HRP was 1:4.

b. The same oxidize antibody was incubated with an oxidized peroxidase-PNATPH conjugate (1 mg/ml protein plus 3.1 mM hydrazide) with 1:4 molar ratio of IgG to HRP.

c. The same oxidized antibody was also incubated with an oxidized peroxidase—PNATPH conjugate (1 mg/ml protein plus 4.3 mM hydrazide), with 1:4 molar ratio of IgG to HRP.

d. The oxidized antibody was first incubated overnight with PNATPH (0.17 μg/ml protein plus 1.1 mM hydrazide) and then with oxidized HRP, with 1:4 molar ratio of IgG to HRP.

e. The oxidized antibody was incubated overnight with PNATPH (0.17 μg/ml protein plus 4 mM hydrazide) and then with oxidized HRP, with 1:4 molar ratio of IgG to HRP.

The HRP-PNATPH-IgG conjugates prepared as described under a-e were tested for their ability to detect the antigen.

Figure 6:
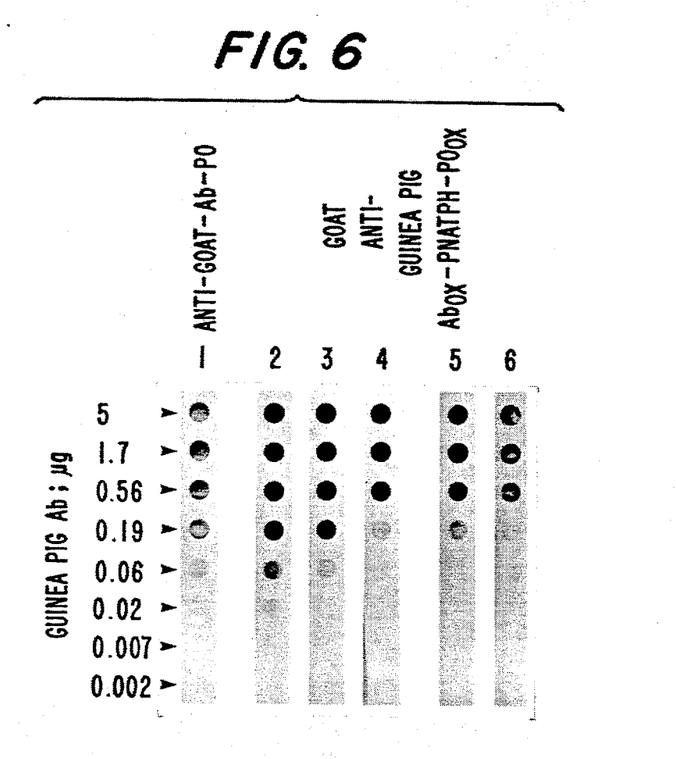
FIG. 6 shows detection of an antigen according to the method of the present invention prepared as described in Examples 5 b-f.

FIG. 6 shows the result of this experiment. A commercial (Sigma) secondary antibody-HRP conjugate was used in lane 1, the conjugate prepared as described under a in lane 2, under b in lane 3, under c in lane 4, under d in lane 5 and under e in lane 6. In all cases the primary antibody concentration was 1 μg/ml.

The results clearly show that two of the conjugates we prepared (lane 3 and 4) show a similar and one a better sensitivity (lane 2) than the commercial conjugate. This is a clear demonstration that such conjugates can be competitive to the conjugates prepared by coupling the enzyme to the protein part of the antibody molecule.

f. In contrast to examples 5d and 5e, the coupling of an enzyme to an antibody-polyhydrazide conjugate can be done also on a solid support. Thus, oxidized goat anti-guinea pig antibody was coupled to PNATPH (4 mM) and then incubated with the membrane containing the antigen. After washing away the unbound IgG—PNATPH, the membrane was incubated with oxidized HRP. The antigen was detected by staining on HRP activity (not shown), but the sensitivity was somewhat lower than shown in FIG. 6, lane 2.

EXAMPLE 6

A novel approach for detection of antigens bound to a solid phase a. In this approach all reactions are carried out on a solid phase (membrane). First, an antigen is immobilized to a solid support. Second, an oxidized antibody binds to this antigen. Third, a polyhydrazide is coupled to the sugar part of the antibody molecule. Fourth, an oxidized glycoenzyme is coupled to the polyhydrazide and the antigen then detected through a product of the enzyme reaction.

Figure 7:
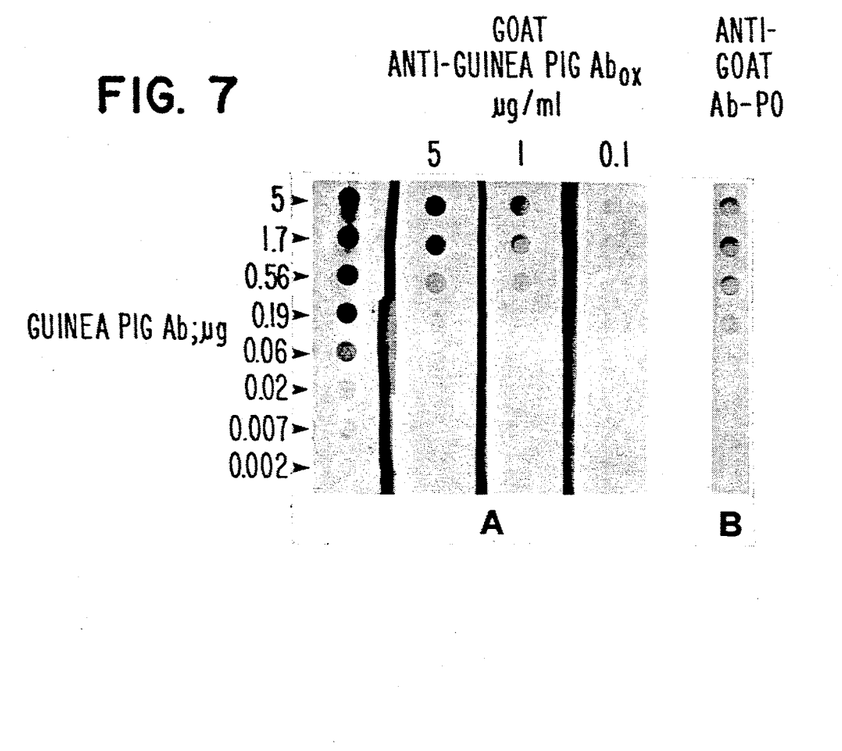
FIG. 7 shows another detection of an antigen according to the method of the present invention in which all reactions were carried out on a membrane.

FIG. 7 shows detection of an antigen (guinea pig immunoglobulins) according to the reaction sequence outlined above. The first nitrocellulose membrane strip was stained with Aurodye. The other three strips (panel A) were incubated with the oxidized (2 mM sodium peridate, 1 h) goat anti-guinea pig antibody at the specified concentrations in BLOTTO pH 7.5 for 1 h. The subsequent incubation with PNATPH and oxidized HRP were done as described in Example 4. Panel B shows detection of the same antigen with commercial (Sigma) secondary antibody conjugate. The first antibody concentration was 1 µg/ml and the rabbit anti-goat antibody-HRP conjugate was diluted 1:400 with BLOTTO.

The antigen can be clearly detected by the new approach (FIG. 7), but the sensitivity is lower than that achieved with the commercial conjugate or demonstrated in Example 5.

b. We assume that the sensitivity of detection of an antigen by the new approach is limited by the sensitivity of detection of IgG by our glycoprotein staining procedure. This assumption is supported by the results shown in FIG. 8.

Figure 8:
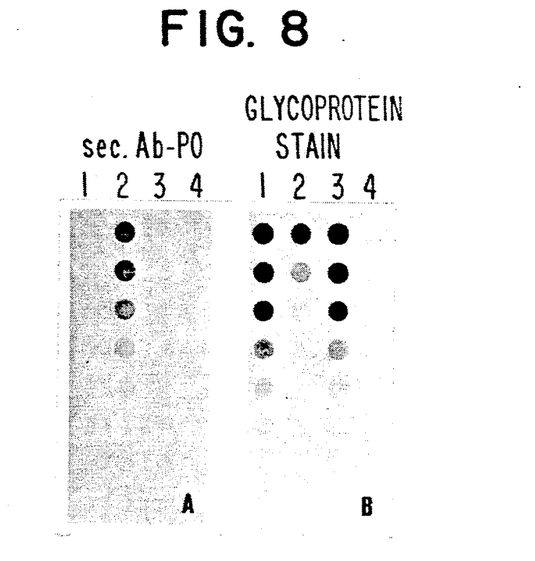
FIG. 8 shows comparative results on sensitivity of antigen and glycoprotein detection using the method of the present invention as described in Example 6 b.

Panel A and B contained the same four proteins, including fetuin (lane 1), rabbit IgG (lane 2), human IgM (lane 3) and beta-galactosidase (lane 4). The membrane in panel A was incubated with goat anti-rabbit antibody-HRP (Sigma, diluted 1:200) in BLOTTO pH 7.5 for 2 h. The membrane in panel B was stained on glycoproteins, as described in Example 4.

FIG. 8 shows that IgG can be detected with about 10 times better sensitivity by means of the commercial secondary antibody conjugate. However, for another class of antibodies, such as IgM shown in lane 3, the glycoprotein staining is more sensitive than secondary antibody staining of IgG (lane 2 panel A verses lane 3 panel B). Thus, this result indicates that monoclonal IgM antibodies will be detected with better sensitivity than IgG. We have also observed that immunoglobulins IgY from chicken give a stronger signal than mammalian IgG with our glycoprotein stain. Therefore, the antibodies raised in avian species appear well suited for detection of antigens according to the new approach provided in this invention. Mammalian IgM and chicken immunoglobulins stain better probably because they contain more carbohydrate. Hence we expect that the new approach will be particularly well applicable to the immunoglobulins containing more sugar than IgG. In spite of its currently lower sensitivity when using IgG class antibodies, the new approach is attractive because it offers the following advantages.

The first advantage of the new approach is that a separate preparation of antibody-enzyme conjugates is not necessary.

The second advantage is that there is no foreign molecule (label) introduced into the antibody prior to binding to an antigen. A label molecule attached to an antibody often adversely affects binding of the labeled antibody to its antigen.

The third advantage of this approach is that secondary antibodies are not necessary. This means that only one animal needs to be sacrificed for preparation of antibodies against one antigen. Further, false positive results and other problems associated with cross-reactions of secondary antibodies are avoided.

The fourth advantage is that it is not necessary to purify an antibody. We have found that desalted rabbit serum, containing antibodies against creatine kinase, can be used after periodate oxidation to detect the antigen by the procedure outlined above. The amount of periodate used was equal to the molar amount of neutral sugars, determined with mannose as a standard (3 umole/ml sugar was found and the oxidation was done with 3 mM $NaIO_4$ for 2 h at 0° C.).

EXAMPLE 7

Application of polyhydrazides labeled with a radioactive compound in detection of glycoproteins Radioactive compounds containing a group that reacts with the hydrazide function can be coupled to the polyhydrazides. As examples, we describe the preparation of PNATPH labeled with oxidized gamma-$^{32}$P-ATP and $^{125}$I labeled Bolton-Hunter reagent. Polymers of high and low specific radioactivity are prepared.

a. PNATPH of lower specific radioactivity was prepared as follows. To a solution of 5 µl of $^{32}$P-ATP (50 µCi) and 5 µl of 0.2M sodium acetate buffer, pH 4.5 cooled to 0° C., freshly prepared $NaIO_4$ (1 µl, 5 mM) was added and the mixture incubated for two hours at 0° C. in the dark. Sodium arsenite (1 µl, 5 mM) was then added and the solution was left for 30–60 min at room temperature. PNATPH (40 µl, 1.5 mM in hydrazide) was added and the reaction mixture left at +4° C. overnight. A small column of Sephadex G-25 (approximately 1 ml) was used to purify the labeled polymer from the unreacted or unoxidized ATP. About 90% of the initial radioactivity was coupled to the polymer.

b. PNATH of higher specific radioactivity was obtained by lowering the ratio of PNATPH to the label. Thus, $^{32}$P-ATP (30 µCi, in 6.5 µl) was oxidized by periodate (3 mM, 1 µl) and incubated with PNATPH (1 µl, 0.4 mM), as described under 5a. After passing of the reaction mixture through a small column of Sephadex G-25, over 90% of the initial radioactivity was found in the high molecular weight fraction.

Figure 9A:
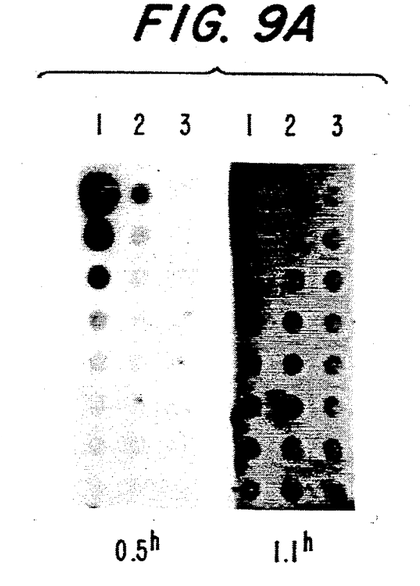
FIGS. 9A and 9B show specific detection of glycoproteins with a polyhydrazide labeled with $^{32}P$ of a low (panel A) or high (panel B) specific radioactivity.
Figure 9B:
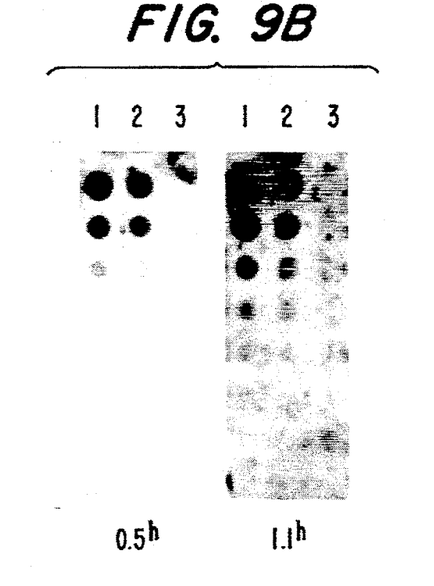

FIG. 9 shows the membranes incubated with $^{32}$P labeled PNATPH of low (panel A) and high (pane B) specific radioactivity. Each membrane was incubated with 0.9 µCi/ml in sodium acetate buffer for the times indicated. The proteins were preoxidized and applied to lane 1 (fetuin), lane 2 (rabbit IgG) and lane 3 (beta—galactosidase) in concentrations given in FIG. 2.

It seems that the coupling of radioactive hydrazide to the oxidized glycoproteins on the membrane is over after 30 min. Longer incubation time produces only more background. The sensitivity is better with the polyhydrazide of lower specific radioactivity, probably because the concentration of the reagent is much higher during the coupling reaction. The overall sensitivity is not better than with the enzyme-labeled polyhydrazides (FIGS. 2–8), but it seems that the signal is more proportional to the amount of glycoproteins.

Polyacrylic hydrazides were also labeled with $^{125}$I.

c. A sample of PANPH, (400 μl, 1.4 mM) prepared as described in Example 2, was added to 140 μCi of Bolton-Hunter reagent (evaporated from dry benzene) and reacted for 2 h in an ice bath. The solution was then passed over a column filled with 7 ml of Amberlite XAD-7 equilibrated in sodium acetate buffer pH 4.5. The column was washed with the same buffer and then with 30% methanol in water. About 50% of the applied radioactivity passed through the column (representing low molecular weight compounds as checked by PD-10 gel filtration) whereas the remaining 50% was eluted with 12 ml of 30% methanol.

Figure 10A:
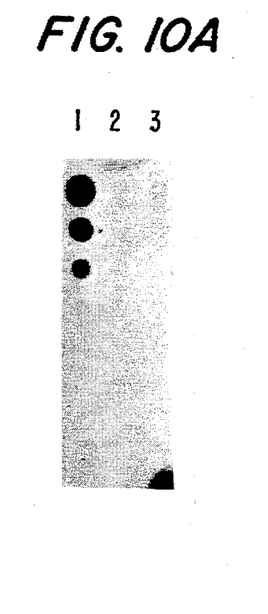
FIGS. 10A-10C show specific detection of glycoproteins with different polyhydrazides labeled with $^{125}I$.
Figure 10B:
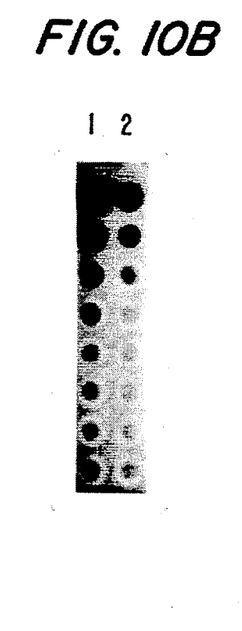
Figure 10C:
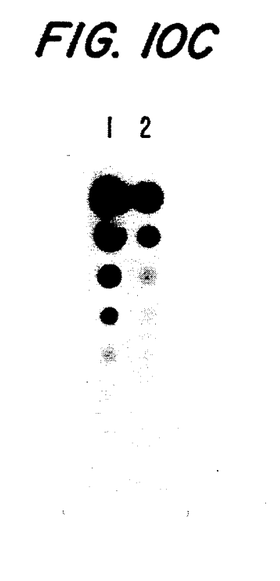

FIG. 10 shows the glycoprotein staining through the $^{125}$I-polyhydrazides. The membrane in panel A was incubated with the labeled PANPH (0.5 μCi/ml) for 2 h and the membrane in panel B was incubated overnight. The membrane in panel C was incubated with the labeled PNATPH for 3 h.

These results demonstrate that a long incubation with the labeled PANPH is necessary to detect IgG (lane 2 in panel B versus lane 2 in panel A). The background staining with PANPH is stronger than with PNATPH, and even after a short incubation (3 h) it is possible to detect IgG with PNATPH (pane C versus panel B). However, the overall sensitivity is not better than the sensitivity achieved with the enzyme-labeled polyhydrazides.

REFERENCES

1. Tijssen, P. (1985) in Practice and Theory of Enzyme Immunoassays, Elsevier, Amsterdam
2. Wilcheck, M., and Bayer, E. A. (1987) Meth. Enzymol. 138, 429
3. Rodwell, J. D., Alvarez, V. L., Lee, C., Lopez, A. D., Goers, J. W. F., King, H. D., Powsner, H. J., and McKearn, T. J. (1986) Proc. Natl. Acad. Sci. 83, 2632
4. Oseroff, A. R., Ohuoha, D., Hansan, T., Bommer, J. C., and Yarmush, M. L. (1986) Proc. Natl. Acad. Sci. 83, 8744
5. O'Shannessy, D., and Quarles, R. H. (1985) J. Appl. Biochem. 7, 347
6. Jeanson, A., Cloes, J. M., Bouchet, M., and Rentier, B. (1988) J. Immunol. Methods 111, 261
7. Heimgartner, U., Kozulic, B., and Mosbach, K. (1988) submitted for publication
8. Pollak, A., Blumenfeld, H., Wax, M., Baughn, R. L., and Whitesides, G. M. (1980) J. Am. Chem. Soc. 102, 6324
9. Kozulic, B., and Mosbach, K. (1987) Patent Application PCTEP88/00515
10. Kozulic, B. (1988) European Patent Application 88810717.4, Priority Date Oct. 19, 1988
11. Johnson, D. A., Gautsch, J. W., Sportsman, J. R., and Elder, J. H. (1984) Gene Anal. Techn. 1, 3
12. Bourne, J. A. (1983) in Handbook of Immunoperoxidase Staining Methods, pp 21–22, DAKO Corporation, Santa Barbara
13. Kozulic, B., Leustek, I., Pavlovic, B., Mildner, P., and Barbaric, S. (1987) Appl. Biochem. Biotech. 15, 265
14. Bury, A. F. (1981) J. Chromatogr. 213, 491
15. Towbin, H., Staehelin, T., and Gordon, J. (1979) Proc. Natl. Acad. Sci. 76, 4350
16. Morrissey, J. H. (1981) Anal. Biochem. 117, 307

We claim:

1. A method for detection of an oxidized glycoprotein comprising the steps of:
    a) binding a glycoprotein to a solid support;
    b) oxidizing the bound glycoprotein with periodate to form an oxidized glycoprotein wherein aldehyde or ketone groups are formed by oxidizing carbohydrate residues of said glycoprotein;
    c) reacting said oxidized glycoprotein with a polyacrylic polyhydrazide wherein said polyacrylic polyhydrazide binds to said oxidized glycoprotein, and wherein said polyacrylic polyhydrazide is a copolymer comprising repeating units possessing a hydrazide group and repeating units possessing hydroxyl groups;
    d) reacting a label with said polyacrylic polyhydrazide, wherein said label contains aldehyde groups or activated ester groups which bind to said polyacrylic polyhydrazide through hydrazide groups on said polyacrylic polyhydrazide; and
    e) detecting said oxidized glycoprotein bound to said support through detection of said polyacrylic polyhydrazide having said label bound thereto.

2. The method of claim 1 wherein said label is bound to said polyacrylic polyhydrazide before said polyacrylic polyhydrazide is reacted with said oxidized glycoprotein.

3. The method of claim 1, wherein said glycoprotein is directly bound to said solid support.

4. The method of claim 3, wherein said solid support is a membrane.

5. The method of claim 3, wherein said label is a glycoenzyme with oxidized sugar chains, and wherein said oxidized sugar chains of said label are coupled to said oxidized glycoprotein by means of said polyacrylic polyhydrazide.

6. The method of claim 3, wherein said label is a radioactive compound containing aldehyde groups or activated ester groups, and wherein said radioactive compound is bound to said polyacrylic polyhydrazide through said aldehyde groups or said activated ester groups.

7. The method of claim 1, wherein said glycoprotein is bound to said solid support through another molecule.

8. The method of claim 7, wherein said solid support is a membrane.

9. The method of claim 7, wherein said glycoprotein is bound to said solid support through an antigen.

10. The method of claim 9, wherein said glycoprotein is an antibody.

11. The method of claim 7, wherein the label is a glycoenzyme with oxidized sugar chains, and wherein the oxidized sugar chains of said label are coupled to the oxidized sugar chains of the oxidized glycoprotein by means of said polyacrylic polyhydrazide.

12. The method of claim 7, wherein said label is a radioactive compound containing aldehyde groups or activated ester groups, and wherein said radioactive compound is bound to said polyacrylic polyhydrazide through said aldehyde groups or said activated ester groups.

13. A method for detection of an oxidized glycoprotein comprising the steps of:

a) oxidizing a glycoprotein with periodate to form an oxidized glycoprotein wherein aldehyde or ketone groups are formed by oxidizing carbohydrate residues of said glycoprotein;

b) binding said oxidized glycoprotein to a solid support;

c) reacting said oxidized glycoprotein with a polyacrylic polyhydrazide wherein said polyacrylic polyhydrazide binds to said oxidized glycoprotein, and wherein said polyacrylic polyhydrazide is a copolymer comprising repeating units possessing a hydrazide group and repeating units possessing hydroxyl groups;

d) reacting a label with said polyacrylic polyhydrazide, wherein said label contains aldehyde groups or activated ester groups which bind to said polyacrylic polyhydrazide through hydrazide groups on said polyacrylic polyhydrazide; and e) detecting said oxidized glycoprotein bound to said support through detection of said polyacrylic polyhydrazide having said label bound thereto.

14. The method of claim 13 wherein said label is bound to said polyacrylic polyhydrazide before said polyacrylic polyhydrazide is reacted with said oxidized glycoprotein.

* * * * *